US010765827B2

(12) United States Patent
Baiko (10) Patent No.: US 10,765,827 B2
(45) Date of Patent: Sep. 8, 2020

(54) MAGNETICALLY CONTROLLED FOREHEAD SUPPORT

(71) Applicant: KONINKLIJKE PHILIPS N.V., Eindhoven (NL)

(72) Inventor: Robert William Baiko, Pittsburgh, PA (US)

(73) Assignee: Koninklijke Philips N.V., Eindhoven (NL)

( * ) Notice: Subject to any disclaimer, the term of this patent is extended or adjusted under 35 U.S.C. 154(b) by 211 days.

(21) Appl. No.: 15/935,357

(22) Filed: Mar. 26, 2018

(65) Prior Publication Data

US 2018/0280648 A1  Oct. 4, 2018

Related U.S. Application Data

(60) Provisional application No. 62/477,600, filed on Mar. 28, 2017.

(51) Int. Cl.
*A61M 16/06* (2006.01)

(52) U.S. Cl.
CPC ........ *A61M 16/0611* (2014.02); *A61M 16/06* (2013.01); *A61M 16/0605* (2014.02); *A61M 16/0616* (2014.02); *A61M 16/0644* (2014.02); *A61M 16/0633* (2014.02); *A61M 16/0683* (2013.01); *A61M 2205/0272* (2013.01)

(58) Field of Classification Search
CPC .......... A61M 16/0493; A61M 16/0611; A61M 16/0616; A61M 16/0622; A61M 16/0633; A61M 16/0666; A61M 16/0683; A61M 16/0816; A61M 16/0825; A61M 16/0875; A61M 2205/0272; A61M 2205/12; A61M 2205/43; A61M 2205/581
See application file for complete search history.

(56) References Cited

U.S. PATENT DOCUMENTS

| | | | |
|---|---|---|---|
| 7,793,987 B1* | 9/2010 | Busch | A61M 16/0816 285/9.1 |
| 9,987,451 B2* | 6/2018 | Stegman | A61M 16/06 |
| 10,232,137 B2* | 3/2019 | Romagnoli | A61M 16/0057 |
| 2012/0017901 A1 | 1/2012 | Mainusch | |
| 2015/0250972 A1* | 9/2015 | Haibach | A61M 16/0683 128/202.27 |
| 2015/0352308 A1 | 12/2015 | Cullen | |
| 2019/0175863 A1* | 6/2019 | Hocking | A61M 16/0666 |

FOREIGN PATENT DOCUMENTS

WO  WO2006096924 A1  9/2006

\* cited by examiner

*Primary Examiner* — Annette Dixon
(74) *Attorney, Agent, or Firm* — Michael W. Haas (57) ABSTRACT

A patient interface device is for use in a pressure support system delivering a flow of breathing gas to an airway of a patient. The patient interface device includes a sealing apparatus having a cushion structured to sealingly engage about the airway of the patient and defining a passage therethrough which is structured to receive the flow of breathing gas. A first magnetic material is coupled to the cushion, and a second magnetic material coupled to the cushion or another element of the sealing apparatus. The second magnetic material and the first magnetic material are configured such that there is a repulsive magnetic force therebetween. The coupling of the first magnetic material and the second magnetic material provides an adjustable coupling that provides selective adjustment of the magnitude of the repulsive magnetic force.

18 Claims, 6 Drawing Sheets

MAGNETICALLY CONTROLLED FOREHEAD SUPPORT

CROSS-REFERENCE TO RELATED APPLICATIONS

This patent application claims the priority benefit under 35 U.S.C. § 119(e) of U.S. Provisional Application No. 62/477,600 filed on Mar. 28, 2017, the contents of which are herein incorporated by reference.

BACKGROUND OF THE INVENTION

1. Field of the Invention

The present invention relates to patient interface devices. The present invention also relates to pressure support systems including patient interface devices.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component having a soft, flexible sealing cushion on the face of the patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is typically secured to the patient's head by a headgear component. The patient interface device is connected to a gas delivery tube or conduit and interfaces the pressure support device with the airway of the patient, so that a flow of breathing gas can be delivered from the pressure/flow generating device to the airway of the patient.

One drawback of known patient interface devices is that during therapy, leaks often form between the cushion and the face of the patient. Another drawback is that during therapy, red marks often form on the face of the patient. Prior proposals to address these problems typically increase the force with which the patient interface device presses into the face via the headgear, but are inadequate because many patients require a tighter, and more comfortable seal in certain localized regions of their face.

SUMMARY OF THE INVENTION

Accordingly, it is an object of the present invention to provide an improved patient interface device and pressure support system including the same.

As one aspect of the disclosed concept, a patient interface device is provided for use in a pressure support system delivering a flow of breathing gas to an airway of a patient. The patient interface device comprises a sealing apparatus comprising a cushion structured to sealingly engage about the airway of the patient and defining a passage therethrough which is structured to receive the flow of breathing gas; a first magnetic material coupled to the cushion; and a second magnetic material coupled to one of the cushion or another element of the sealing apparatus. The second magnetic material and the first magnetic material are configured such that there is a repulsive magnetic force therebetween. The repulsive magnetic force has a magnitude. The coupling of at least one of the first magnetic material and the second magnetic material is an adjustable coupling which provides for selective adjustment of the magnitude of the repulsive magnetic force.

As another aspect of the disclosed concept, a pressure support system comprises a gas flow generator structured to generate a flow of breathing gas to be delivered to an airway of a patient; a conduit coupled to the gas flow generator; and the aforementioned patient interface device.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly (i.e., one part is positioned in or directly on another part) or indirectly (i.e., through one or more intermediate parts or components), so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the phrase "adjustably coupled" shall mean that two components are coupled together in a manner wherein one of the components is movable with respect to the other component. For example and without limitation, a component that is coupled to and rotates with respect to another component is adjustably coupled to the other component. Additionally, a component that is coupled to and slides with respect to another component is likewise adjustably coupled to the other component.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

As used herein, the word "patient" or "user" shall be used interchangeably to refer to the person to which the interface device is delivering a flow of breathing gas. As used herein, two or more elements which interact in a "repulsive manner" are generally repelled away from each other via magnetic forces (e.g., without limitation, two magnets which are arranged having the same poles (i.e., N-N, S-S) facing each other).

As used herein, in arrangements in which repulsive forces are utilized, a "first magnetic material" and a "second magnetic material" include a material that is attracted to iron or steel, e.g., a magnet, and a second material that is repelled from the first material, e.g., a second magnet arranged with a common pole facing the first magnet. It is understood that the purpose of the "first magnetic material" and the "second magnetic material" in such arrangements is to have the two materials magnetically repelled away from each other. Thus, a magnetized material and a non-magnetized materials, e.g. a magnet and a piece of normal steel, are not a "first magnetic material" and a "second magnetic material" in such arrangements.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
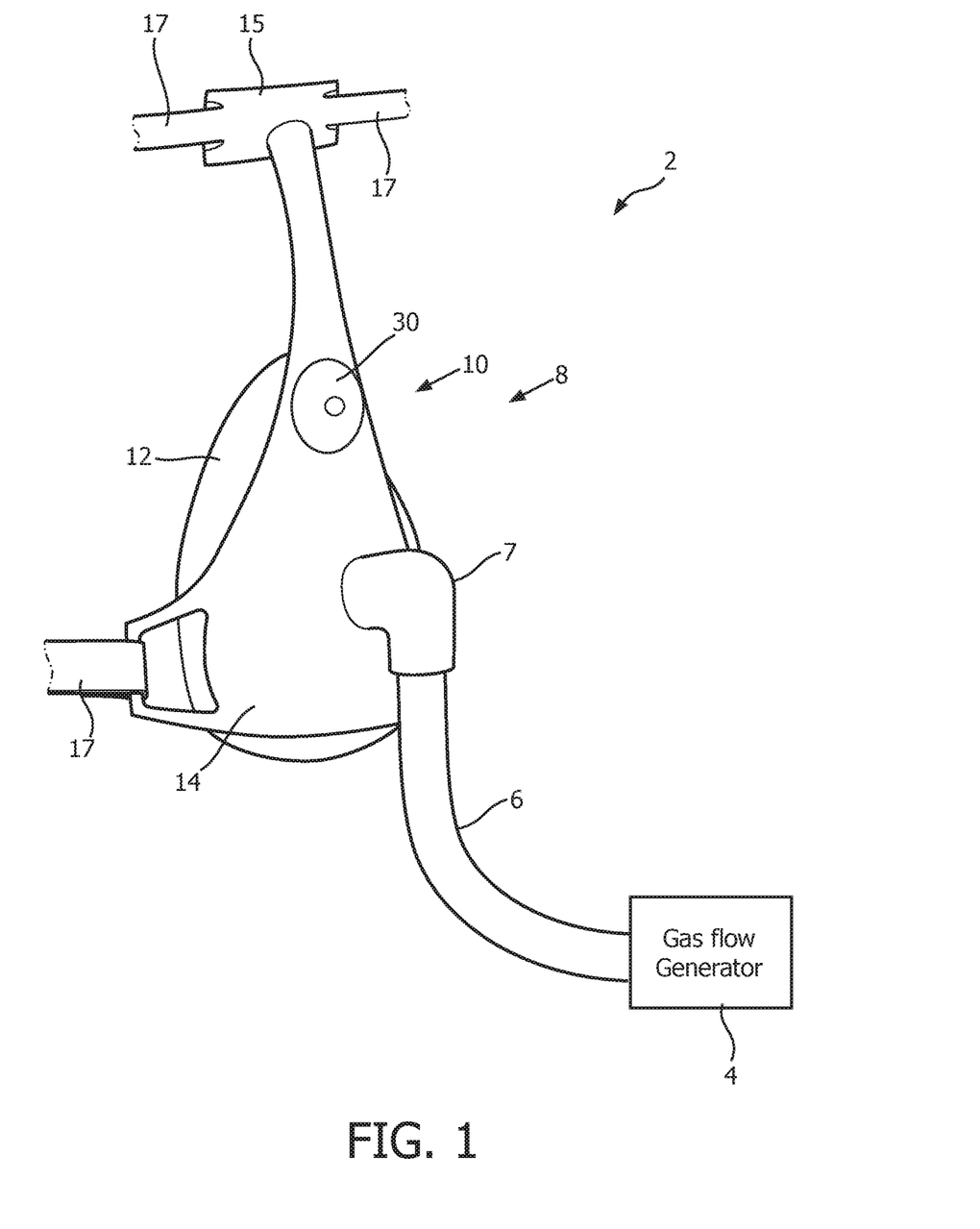
FIG. 1 is a simplified isometric view of a pressure support system, in accordance with one non-limiting embodiment of the disclosed concept.

FIG. 1 is a simplified view of a pressure support system 2, in accordance with one non-limiting embodiment of the disclosed concept. Pressure support system 2 includes a gas flow generator 4 (shown schematically), a conduit (e.g., without limitation, hose 6) coupled to gas flow generator 4, an elbow member 7 coupled to hose 6, and a patient interface device 8. Patient interface device 8 includes a sealing apparatus 10 having a cushion 12, a frame 14 coupled to elbow 7 and cushion 12, a forehead support 15 coupled to frame 14, and a headgear (see, for example, portions of headgear straps 17, shown in FIG. 1) coupled to frame 14 and forehead support 15.

Gas flow generator 4 is structured to generate a flow of breathing gas to be delivered to an airway of a patient. More specifically, when patient interface device 8 is donned by the patient and pressure support therapy is being delivered, gas flow generator 4 passes a flow of pressurized breathing gas into hose 6. In one exemplary embodiment, cushion 12 is a full face cushion. However, it will be appreciated that the disclosed concept is applicable to any suitable alternative cushion (e.g., without limitation, nasal and/or pillows style cushions, not shown). Cushion 12 is structured to sealingly engage about an airway of the patient and defines a passage therethrough which is structured to receive the flow of breathing gas from hose 6. That is, cushion 12 is fluidly coupled to hose 6. As a result, the flow of breathing gas is able to be passed from gas flow generator 4 to the patient.

Figure 2:
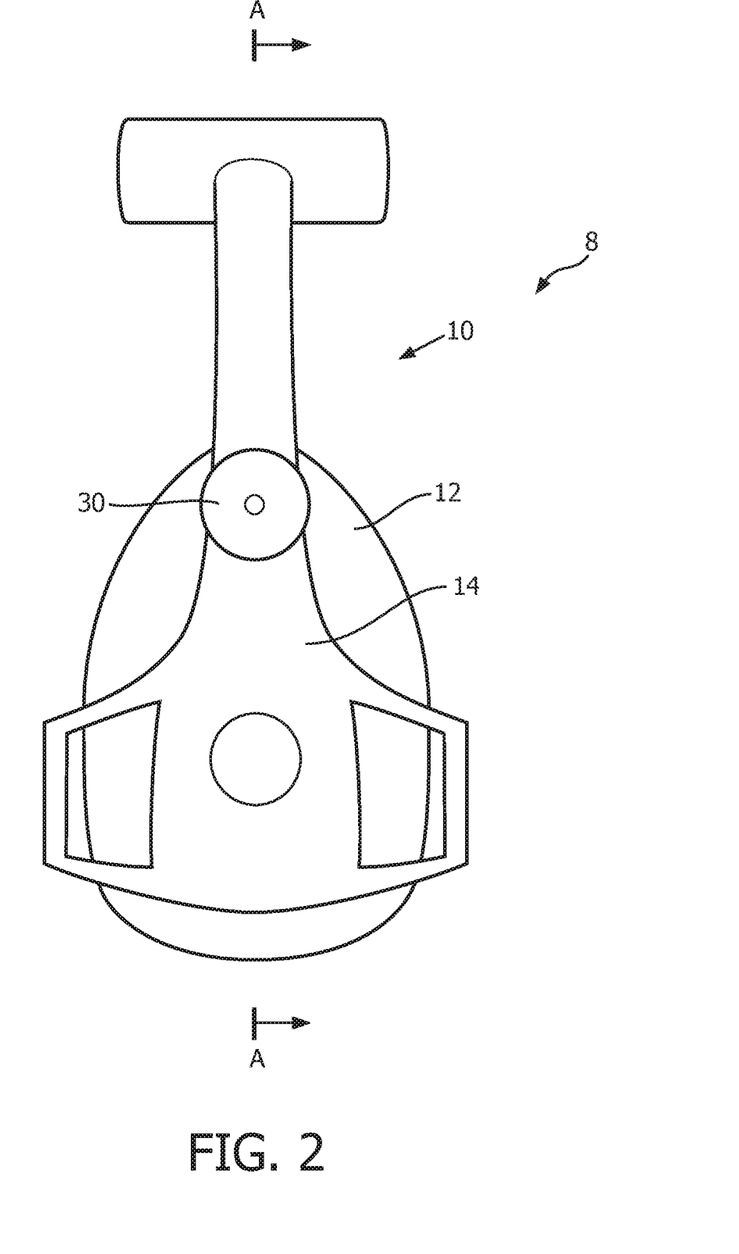
FIG. 2 is a front view of a patient interface device for the pressure support system of FIG. 1.
Figure 3A:
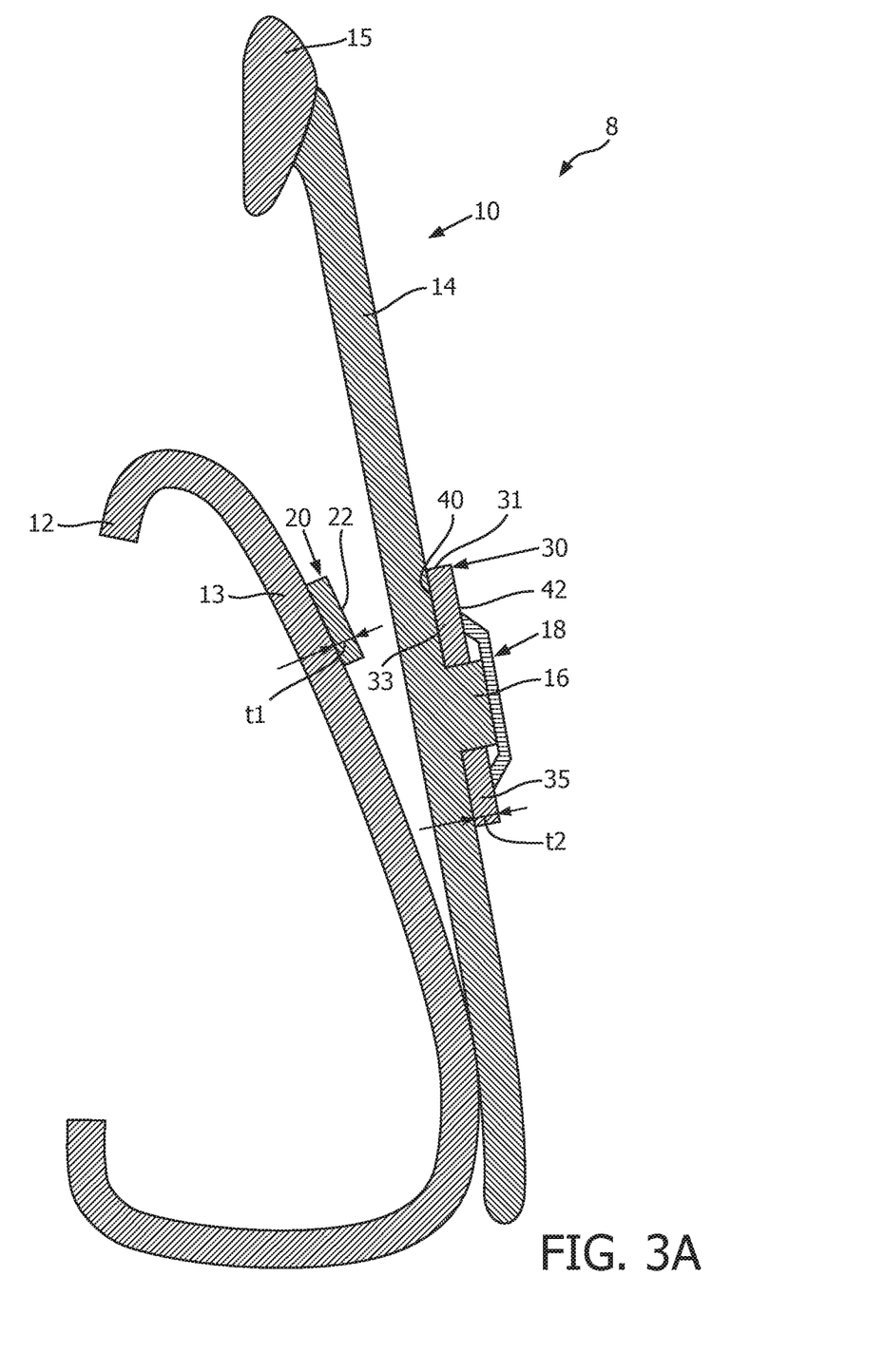
FIG. 3A is a section view of the patient interface device of FIG. 2, taken along line A-A of FIG. 2, shown with a magnetic material in a first position.

FIG. 2 and FIG. 3A show front and section views, respectively, of patient interface device 8. As shown in FIG. 3A, patient interface device 8 further includes a first magnetic material 20 and a second magnetic material 30. In the exemplary embodiment of FIGS. 1 through 3B, cushion 12 has a nose bridge region 13 (FIGS. 3A and 3B), and first magnetic material 20 is a typical magnet that is fixedly coupled to nose bridge region 13. In one example embodiment, first magnetic material 20 is connected to nose bridge region 13 by a mechanical mechanism (e.g., without limitation, being glued to, molded to, and/or affixed to nose bridge region 13). It will be appreciated that suitable alternative first magnetic materials are contemplated by the disclosed concept (e.g., a magnetic material having portions with different strength charges). Second magnetic material 30 is a magnet having portions with different strength charges, and is adjustably coupled to frame 14. In other words, different portions of second magnetic material 30 are structured to repel a given magnetic material differently. Furthermore, referring to FIG. 3A, frame 14 has a protrusion 16 extending through second magnetic material 30, and patient interface device 8 further includes a retaining member 18 secured to protrusion 16 in order to adjustably couple second magnetic material 30 to frame 14. In the exemplary embodiment, second magnetic material is rotatably coupled to frame 14. In accordance with the disclosed concept, first magnetic material 20 and second magnetic material 30 are oriented such that there is a repulsive magnetic force therebetween. That is, in the position depicted in FIG. 3A, the repulsive magnetic force between first magnetic material 20 and second magnetic material 30 is such that there is a force on cushion 12 to the left, and a force on frame 14 to the right.

Figure 4:
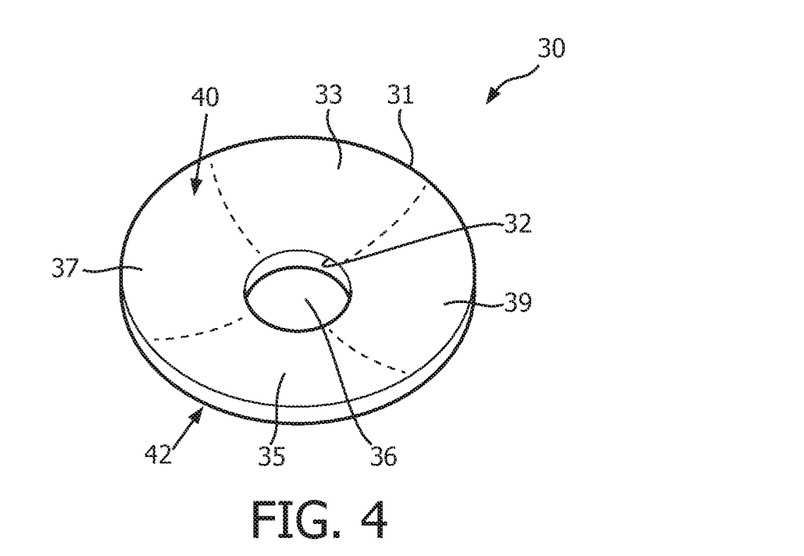
FIG. 4 is an isometric view of a magnetic material for the patient interface device of FIGS. 3A and 3B.

FIG. 4 shows a simplified view of second magnetic material 30. As shown, second magnetic material 30 has a peripheral edge 31 and an inner edge 32 defining a thru hole 36. In the exemplary embodiment, second magnetic material 30 is a magnet in an annulus shape that is a unitary component. In one exemplary embodiment, second magnetic material 30 is formed by magnetic force manipulation or charging with a magnetic field generator/charger (not shown). However, it is contemplated that a suitable alternative second magnetic material may have any suitable alternative geometry, and/or may be comprised of separate segmented sections that are separately coupled together, without departing from the scope of the disclosed concept. Continuing to refer to FIG. 4, second magnetic material 30 further has a plurality of portions (portions 33,35,37,39 are shown separated by dashed lines in FIG. 4) each extending from proximate inner edge 32 to proximate peripheral edge 31. In the exemplary embodiment, second magnetic material 30 has a first generally planar surface 40, a generally planar second surface 42 opposite and parallel to first surface 40, and portions 33,35,37,39 are each separate regions of first surface 40. It will, however, be appreciated that other suitable alternative geometries and/or configurations of a magnetic material are contemplated by the disclosed concept.

Furthermore, portions 33,35,37,39 are each structured to generate different repulsive magnetic forces when aligned with the same region of a given magnetic material. More specifically, in the exemplary embodiment, portions 33,35, 37,39 each have charges that have different magnetic strengths from each other. By having separate magnitudes for each portion, second magnetic material 30 need only be rotated to apply different repulsive forces on first magnetic material 20. Additionally, in accordance with the disclosed concept, cushion 12 is structured to be articulable with respect to frame 14. That is, at least a portion of cushion 12 is movable (e.g., without limitation, pivotable) with respect to frame 14. This advantageously allows for selective adjustment of the magnitude of the force with which cushion 12 presses into the face of the patient, as will be discussed below.

Referring again to FIG. 3A, in one exemplary embodiment, a desired portion/region (i.e., a portion between peripheral edge 31 and inner edge 32) of second magnetic material 30 is aligned with first magnetic material 20. Stated differently, first magnetic material 20 has a center region 22 and second magnetic material 30 has a center region (i.e., proximate thru hole 36) offset (i.e., when viewed from a front view, as shown in FIG. 2) from center region 22 of first magnetic material 20. This configuration, and the adjustable coupling (i.e., rotatable coupling) of second magnetic material 30, advantageously allows for the magnitude of the repulsive magnetic force between first magnetic material 20 and second magnetic material 30 to be adjustable, as will be discussed below. While there is an adjustable coupling between second magnetic material 30 and frame 14 in the exemplary embodiment, it is within the scope of the disclosed concept for the coupling of either or both of first magnetic material 20 and second magnetic material 30 to be an adjustable coupling which provides for the selective adjustment of the magnitude of the repulsive magnetic force between first magnetic material 20 and second magnetic material 30. Additionally, while first magnetic material 20 is a typical magnet and second magnetic material 30 is a magnet having portions (i.e., portions 33,35,37,39) with charges of different strengths, it is contemplated by the disclosed concept that either or both of the first and second magnetic materials may be typical and/or variable magnets, provided the coupling of at least one of the first and second magnetic materials is an adjustable coupling.

Figure 3B:
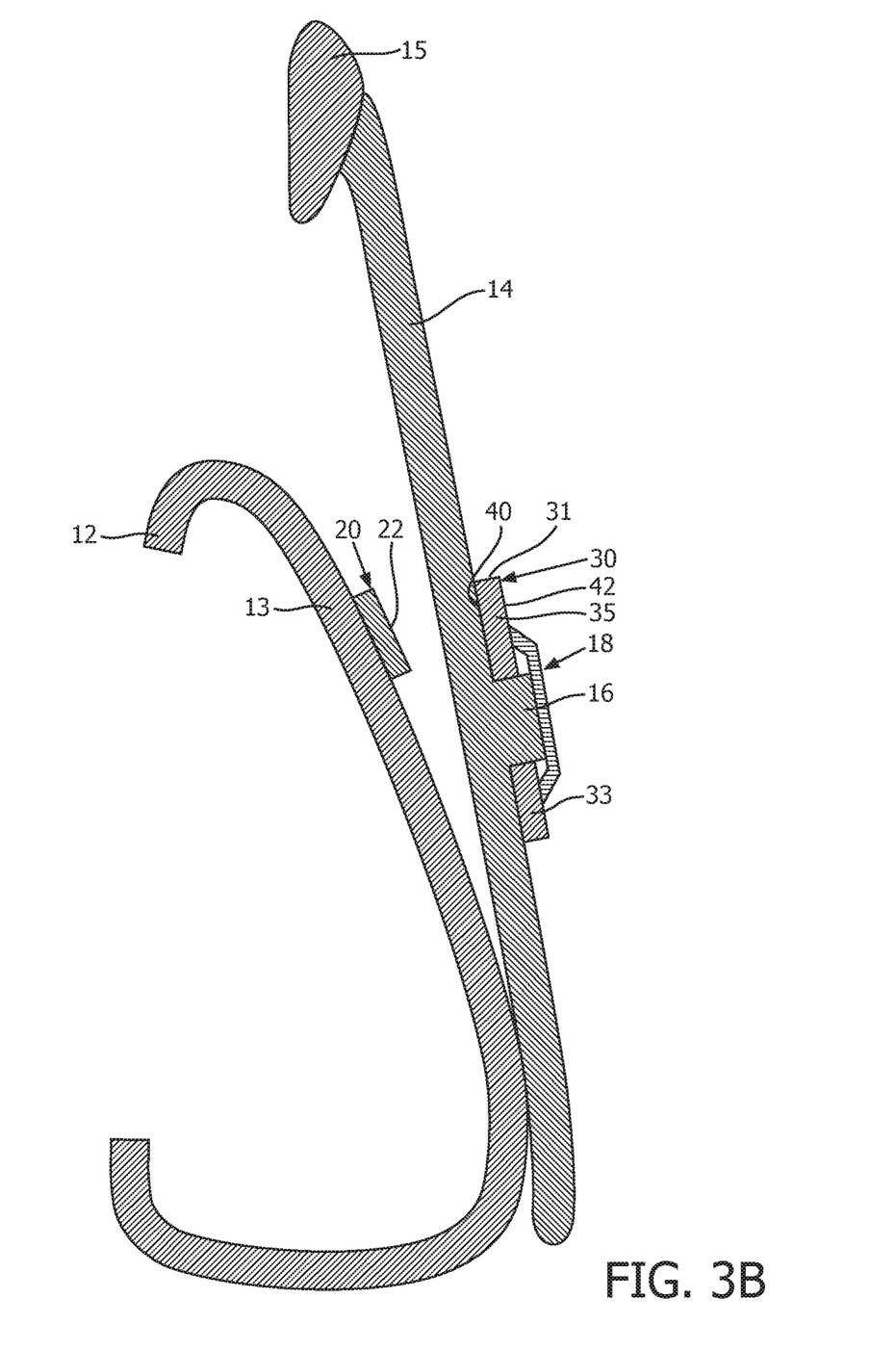
FIG. 3B is a section view of the patient interface device of FIG. 2, taken along line A-A of FIG. 2, shown with a magnetic material in a second position rotated 180 degrees, as compared to its position in FIG. 3A.

Continuing to refer to FIG. 3A, it will be appreciated that portion 33 of second magnetic material 30 is aligned with center region 22 of first magnetic material 20. Stated differently, portion 33 has a geometric center positioned proximate center region 22 and/or closer to center region 22 than any other portion of second magnetic material 30. In this configuration, there is a first repulsive magnetic force between portion 33 of second magnetic material 30 and center region 22 of first magnetic material 20. FIG. 3B shows patient interface device 8 with second magnetic material 30 rotated 180 degrees, as compared to its position in FIG. 3A. In this configuration, portion 35 of second magnetic material 30 is aligned with center region 22 of first magnetic material 20. Stated differently, portion 35 has a geometric center positioned proximate center region 22 and/or closer to center region 22 than any other portion of second magnetic material 30. In this configuration, there is a second repulsive magnetic force between portion 35 and center region 22 of first magnetic material 20.

The magnitude of this second repulsive magnetic force is greater than the magnitude of the first repulsive magnetic force between portion 33 and first magnetic material 20 (i.e., when portion 33 is aligned with center region, FIG. 3A), discussed above. The reason for this is that when second magnetic material 30 is manufactured, the different portions 33,35,37,39 have different magnetic fields that each extend off of first surface 40 a different amount. For example, certain portions could have a relatively tight magnetic field that does not extend off of first surface 40 a large distance, while other portions could have relatively loose magnetic fields that do extend off of first surface 40 a relatively large distance. Furthermore, although not shown, it will be appreciated that when portions 37,39 are each aligned with center region 22 of first magnetic material 20, there is a respective repulsive magnetic force between a respective one of portions 37,39 and center region 22. Additionally, each of the magnitudes of these respective repulsive magnetic forces are different from each other.

In this manner, the repulsive magnetic force between first magnetic material 20 and second magnetic material 30 is selectively adjustable by rotating second magnetic material 30. This provides advantages to patients in terms of improved comfort and improved sealing capabilities. More specifically, the magnitude of the repulsive magnetic force between first magnetic material 20 and second magnetic material 30 is directly proportional to the tightness of the seal between cushion 12 and the face of the patient. For example, a large repulsive magnetic force corresponds to a tighter seal while a weak repulsive magnetic force corresponds to a less tight seal. As such, magnetic materials 20,30 provide a novel mechanism to adjust the force between cushion 12 and the face of the patient, in addition to the mechanism provided by the headgear (see, for example, headgear straps 17 in FIG. 1). Accordingly, the patient may align the weaker magnetic portions of second magnetic material 30 with first magnetic material 20 for a less tight seal, and align the stronger magnetic portions of second magnetic material 30 with first magnetic material 20 for a tighter seal. Stated differently, if a patient who has donned patient interface device 8 desires a tighter seal, the patient can rotate second magnetic material 30 so that the given repulsive magnetic force between first magnetic material 20 and second magnetic material 30 is relatively large (i.e., to the position depicted by FIG. 3B). Conversely, if a patient desires a less tight seal, the patient can rotate second magnetic material 30 so that the given repulsive magnetic force between first magnetic material 20 and second magnetic material 30 is relatively small (i.e., to the position depicted by FIG. 3A).

Additionally, incorporating first magnetic material 20 and second magnetic material 30 advantageously does not detract from the low-profile nature of patient interface device 8. More specifically, as shown in FIG. 3A, first magnetic material 20 and second magnetic material 30 each have a respective thickness $t_1, t_2$. Thicknesses $t_1, t_2$ are preferably less than 2 millimeters.

Although the disclosed concept has been described in association with second magnetic material 30 being coupled to frame 14, it is within the scope of the disclosed concept for a first magnetic material and a second magnetic material to each be coupled to different regions of a cushion, with at least one of the couplings being an adjustable coupling in order to provide for selective adjustment of the magnitude of any repulsive magnetic force therebetween.

Figure 5:
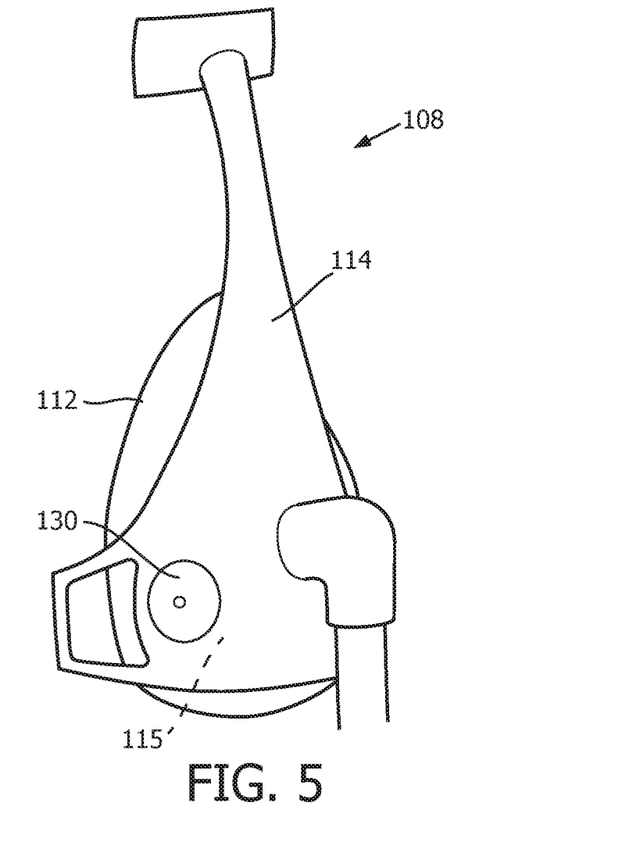
FIG. 5 is a simplified isometric view of another patient interface device, in accordance with another non-limiting embodiment of the disclosed concept.
Figure 6:
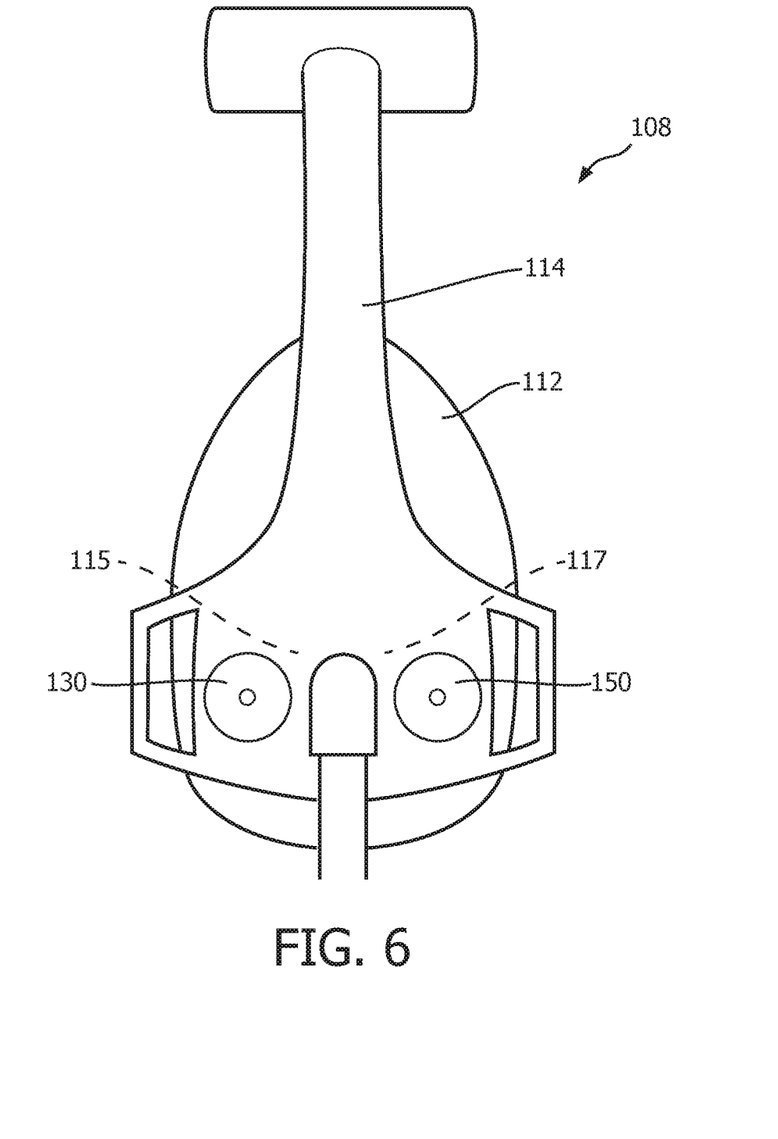
FIG. 6 is a front view of the patient interface device of FIG. 5.

FIG. 5 and FIG. 6 show isometric and front views, respectively, of another patient interface device 108, in accordance with another non-limiting embodiment of the disclosed concept. Patient interface device 108 is similar to patient interface device 8, discussed above, but with some notable differences.

Regarding patient interface device 108, patient interface device 108 includes a cushion 112 and a frame 114 coupled to cushion 112. Cushion 112 includes a first cheek region 115 and a second cheek region 117 (FIG. 6) opposite first cheek region 115. Additionally, patient interface device 108 includes a first magnetic material (not shown) coupled to first cheek region 115, a second magnetic material 130 coupled to frame 114 and being structured to be aligned with first magnetic material (not shown) such that there is a repulsive magnetic force therebetween, a third magnetic material (not shown) coupled to second cheek region 117, and a fourth magnetic material 150 coupled to frame 114 and being structured to be aligned with third magnetic material (not shown) such that there is a repulsive magnetic force therebetween.

First and third magnetic materials (not shown) of patient interface device 108 are structured substantially the same as first magnetic material 20, discussed above. Second and fourth magnetic materials 130,150 are structured substantially the same as second magnetic material 30, discussed above. Accordingly, patient interface device 108 provides advantages in terms of improved seal and improved comfort proximate cheek regions 115,117 by having selective adjustment of at least one of the couplings of first (not shown), second 130, third (not shown), and fourth 150 magnetic materials in order to provide selective adjustment of the magnitude of the repulsive magnetic force between first (not shown) and second 130 magnetic materials of patient interface device 108, as well as between third (not shown) and fourth 150 magnetic materials of patient interface device 108.

Additionally, similar suitable alternative patient interface devices are contemplated by the disclosed concept. For example and without limitation, it is within the scope of the disclosed concept for a first magnetic material (not shown) to be coupled to a chin region of one of cushions 12,112 or a suitable alternative cushion (not shown), and a second magnetic material (not shown) to be could be coupled to frame 14,114 or a suitable alternative frame (not shown), with the repulsive magnetic force interaction being the same as the one between first and second magnetic materials 20, 30.

Accordingly, it will be appreciated that the disclosed concept provides for an improved (e.g., without limitation, more comfortable and better able to provide a seal) patient interface device 8,108 and pressure support system 2 include the same.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device for use in a pressure support system delivering a flow of breathing gas to an airway of a patient, the patient interface device comprising:
   a sealing apparatus comprising a frame and a cushion, the cushion being structured to sealingly engage about the airway of the patient and defining a passage therethrough which is structured to receive the flow of breathing gas, wherein the cushion is affixed to the frame and is structured to pivot with respect to the frame while remaining affixed to the frame;
   a first magnetic material coupled to the cushion; and a second magnetic material coupled to the frame, wherein the second magnetic material has a first portion and a second portion each configured to be aligned with a region of the first magnetic material, wherein the first portion is provided with first charges and has a first magnetic strength of a first magnitude and the second portion is provided with second charges and has a second magnetic strength of a second magnitude that is greater than the first magnitude, wherein the second magnetic material is adjustably coupled to the frame to enable either the first portion or the second portion to be selectively aligned with the region, wherein when the first portion is aligned with the region, there is a first repulsive magnetic force between the first magnetic material and the second magnetic material that causes the cushion to pivot with respect to the frame by a first amount while remaining attached to the frame, and wherein when the second portion is aligned with the region, there is a second repulsive magnetic force between the first magnetic material and the second magnetic material that is greater than the magnitude of the first repulsive magnetic force and that causes the cushion to pivot with respect to the frame by a second amount that is greater than the first amount while remaining attached to the frame.

2. The patient interface device according to claim 1, wherein the second magnetic material further has a plurality of other portions each configured to be aligned with the region of the first magnetic material; wherein, when each of the respective plurality of other portions is aligned with the region, there is a respective repulsive magnetic force therebetween; and wherein the magnitudes of each of the respective repulsive magnetic forces are different from each other.

3. The patient interface device according to claim 2, wherein the second magnetic material has a peripheral edge and an inner edge defining a thru hole; and wherein the first portion, the second portion, and the plurality of other portions each extend from proximate the inner edge to proximate the peripheral edge, and wherein the second magnetic material has an annulus shape and wherein the first portion, the second portion, and the plurality of other portions are spaced about a circumference of the second magnetic material.

4. The patient interface device according to claim 2, wherein the second magnetic material is a unitary component.

5. The patient interface device according to claim 1, wherein the second magnetic material is rotatably coupled to the frame.

6. The patient interface device according to claim 5, wherein the first magnetic material has a center, wherein the second magnetic material has a center, and wherein the center of the first magnetic material is offset with respect to the center of the second magnetic material.

7. The patient interface device according to claim 1, wherein each of the first magnetic material and the second magnetic material has a thickness of less than 2 millimeters.

8. The patient interface device according to claim 1, wherein the cushion comprises a nose bridge region; and wherein the first magnetic material is coupled to the nose bridge region.

9. The patient interface device according to claim 1, wherein the cushion comprises a first cheek region and a second cheek region opposite the first cheek region; wherein the first magnetic material is coupled to the first cheek region; wherein the patient interface device further comprises a third magnetic material and a fourth magnetic material; wherein the third magnetic material is coupled to the second cheek region; wherein the fourth magnetic material is coupled the frame; wherein the fourth magnetic material and the third magnetic material are configured such that there is a repulsive magnetic force therebetween; wherein the repulsive magnetic force between the third magnetic material and the fourth magnetic material has a magnitude; and wherein the coupling of at least one of the third magnetic material and the fourth magnetic material is an adjustable coupling which provides for selective adjustment of the magnitude of the repulsive magnetic force between the third magnetic material and the fourth magnetic material.

10. A pressure support system comprising:
 (a) a gas flow generator structured to generate a flow of breathing gas to be delivered to an airway of a patient;
 (b) a conduit coupled to the gas flow generator, and
 (c) a patient interface device comprising:
  (1) a sealing apparatus comprising a frame and a cushion, the cushion being structured to sealingly engage about the airway of the patient and defining a passage therethrough which is structured to receive the flow of breathing gas, wherein the cushion is affixed to the frame and is structured to pivot with respect to the frame while remaining affixed to the frame, and wherein the cushion is fluidly coupled to the conduit,
  (2) a first magnetic material coupled to the cushion, and
  (3) a second magnetic material coupled to the frame, wherein the second magnetic material has a first portion and a second portion each configured to be aligned with a region of the first magnetic material, wherein the first portion is provided with first charges and has a first magnetic strength of a first magnitude and the second portion is provided with second charges and has a second magnetic strength of a second magnitude that is greater than the first magnitude, wherein the second magnetic material is adjustably coupled to the frame to enable either the first portion or the second portion to be selectively aligned with the region, wherein when the first portion is aligned with the region, there is a first repulsive magnetic force between the first magnetic material and the second magnetic material that causes the cushion to pivot with respect to the frame by a first amount while remaining attached to the frame, and wherein when the second portion is aligned with the region, there is a second repulsive magnetic force between the first magnetic material and the second magnetic material that is greater than the magnitude of the first repulsive magnetic force and that causes the cushion to pivot with respect to the frame by a second amount that is greater than the first amount while remaining attached to the frame.

11. The pressure support system according to claim 10, wherein the second magnetic material further has a plurality of other portions each configured to be aligned with the region of the first magnetic material; wherein, when each of the respective plurality of other portions is aligned with the region, there is a respective repulsive magnetic force therebetween; and wherein the magnitudes of each of the respective repulsive magnetic forces are different from each other.

12. The pressure support system according to claim 11, wherein the second magnetic material has a peripheral edge and an inner edge defining a thru hole; and wherein the first portion, the second portion, and the plurality of other portions each extend from proximate the inner edge to proximate the peripheral edge.

13. The pressure support system according to claim 11, wherein the second magnetic material is a unitary component.

14. The pressure support system according to claim 10, wherein the second magnetic material is rotatably coupled to the frame.

15. The pressure support system according to claim 14, wherein the first magnetic material has a center, wherein the second magnetic material has a center, and wherein the center of the first magnetic material is offset with respect to the center of the second magnetic material.

16. The pressure support system according to claim 10, wherein each of the first magnetic material and the second magnetic material has a thickness of less than 2 millimeters.

17. The pressure support system according to claim 10, when the cushion comprises a nose bridge region; and wherein the first magnetic material is coupled to the nose bridge region.

18. The pressure support system according to claim 10, wherein the cushion comprises a first cheek region and a second cheek region opposite the first cheek region; wherein the first magnetic material is coupled to the first cheek region; wherein the patient interface device further comprises a third magnetic material and a fourth magnetic material; wherein the third magnetic material is coupled to the second cheek region; wherein the fourth magnetic material is coupled the frame; wherein the fourth magnetic material and the third magnetic material are configured such that there is a repulsive magnetic force therebetween; wherein the repulsive magnetic force between the third magnetic material and the fourth magnetic material has a magnitude; and wherein the coupling of at least one of the third magnetic material and the fourth magnetic material is an adjustable coupling which provides for selective adjustment of the magnitude of the repulsive magnetic force between the third magnetic material and the fourth magnetic material.

* * * * *